(12) United States Patent
Kulkarni

(10) Patent No.: US 7,877,268 B2
(45) Date of Patent: Jan. 25, 2011

(54) INTELLIGENT PILL BOX

(76) Inventor: Avinash Uttamrao Kulkarni, 36 State Rt. 10 W, Suite E, East Hanover, NJ (US) 07936

( * ) Notice: Subject to any disclaimer, the term of this patent is extended or adjusted under 35 U.S.C. 154(b) by 745 days.

(21) Appl. No.: 10/987,899

(22) Filed: Nov. 12, 2004

(65) Prior Publication Data

US 2007/0272583 A1 Nov. 29, 2007

Related U.S. Application Data

(60) Provisional application No. 60/519,603, filed on Nov. 13, 2003.

(51) Int. Cl.
*G06Q 50/00* (2006.01)
(52) U.S. Cl. ............................................................. 705/2
(58) Field of Classification Search .................. 705/2
See application file for complete search history.

(56) References Cited

U.S. PATENT DOCUMENTS

| | | | | |
|---|---|---|---|---|
| 4,748,600 | A * | 5/1988 | Urquhart | 368/10 |
| 5,347,453 | A * | 9/1994 | Maestre | 705/2 |
| 5,408,443 | A * | 4/1995 | Weinberger | 368/10 |
| 5,823,178 | A * | 10/1998 | Lloyd et al. | 128/200.14 |
| 6,592,005 | B1 * | 7/2003 | Coughlin et al. | 221/129 |
| 6,594,549 | B2 * | 7/2003 | Siegel | 700/241 |
| 7,158,011 | B2 * | 1/2007 | Brue | 340/309.16 |
| 7,236,428 | B1 * | 6/2007 | Morse | 368/10 |
| 7,295,890 | B2 * | 11/2007 | Jean-Pierre | 700/244 |
| 7,366,675 | B1 * | 4/2008 | Walker et al. | 705/2 |
| 7,545,257 | B2 * | 6/2009 | Brue | 340/309.16 |
| 2002/0067270 | A1 * | 6/2002 | Yarin et al. | 340/573.1 |
| 2003/0086338 | A1 * | 5/2003 | Sastry et al. | 368/10 |

OTHER PUBLICATIONS

Cheung, R., et al. "Compliance with Anti-Tuberculous Therapy: A Field Trial of a Pill-Box with a Concealed Electronic Recording Device", European Journal of Clinical Pharmacology: Germany, West, 1988, 35 (4), p. 401-7.*

* cited by examiner

*Primary Examiner*—Luke Gilligan
*Assistant Examiner*—Robert Sorey

(57) ABSTRACT

The invention is an effective solution to the medical non-compliance problem. Reducing patients' non-compliance offers them better health, longer life expectancy, and better quality of life. The solution offers these great benefits at a limited cost and can be applied to many diseases. The invention uses a dispensing scheme to help patients keep track of their medicine usage through a series of light-emitting diode (LED) alarm indicator signals and audio alarm indicator signals. If the patient is not following the treatment that was prescribed to him or her, the system has the ability to send patient compliance information over the telephone to a disease management system.

3 Claims, 13 Drawing Sheets

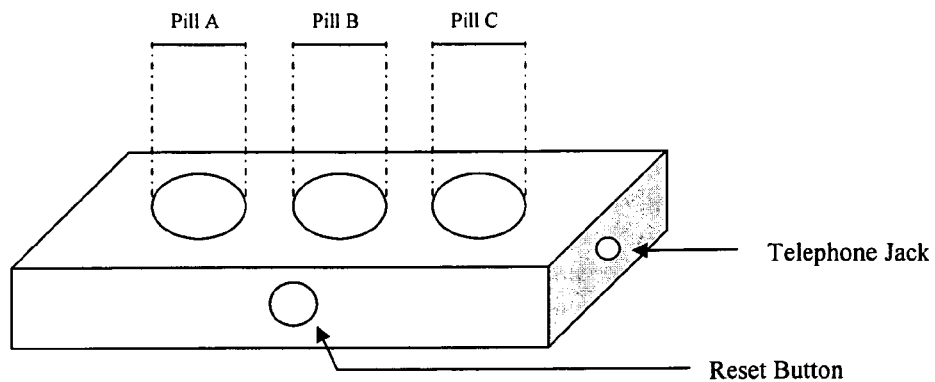
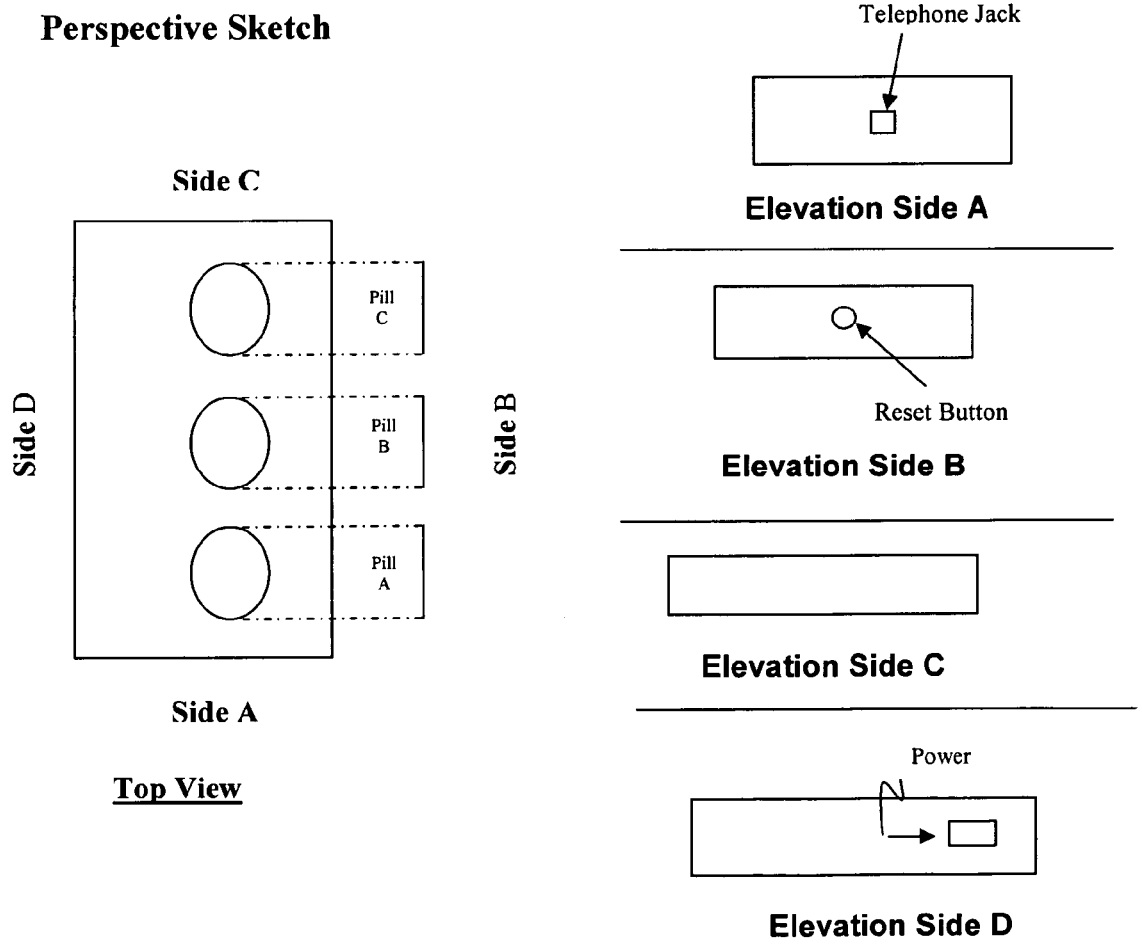
Figure 13

INTELLIGENT PILL BOX

1. CROSS REFERENCE TO RELATED PATENT APPLICATIONS

This application claims the benefit of U.S. Provisional Application No. 60/519,603 filed Nov. 13, 2003.

2. STATEMENT REGARDING FEDERALLY SPONSORED RESEARCH OR DEVELOPMENT

This invention has no Federal Sponsorship.

3. REFERENCE TO A COMPUTER PROGRAM LISTING COMPACT DISK APPENDIX

Computer Program Listing is submitted on a separate Computer Compact Disc (CD). Please refer Appendix B

4. BACKGROUND OF THE INVENTION

Over the past twenty years there have been major advances in medical science. Better techniques and technical equipment have allowed physicians to provide better care and prolong human life as well as improve the standard of that life. Currently, 12.5% of the population of the United States is 65 years of age or older and by 2010 this figure is expected to reach a total of 20% of the population [1]. One of the tools that physicians have available to them to accomplish this task is an expanded array of potent medications. The FDA has approved an average of 340 new medications per for the past several years. According to Emergency Medicine Reports some 90% of people older than 65 years of age take one or more medications per day [1]. The average number of medications by each patient over the age of 60 years in the American Geriatrics Society study was greater than five per day [2].

For maximum effectiveness of these medications to occur, the medications must be taken properly. And while medical science has leaped ahead in many areas one of the problem areas that remain is that of ensuring patient compliance with taking medications.

Compliance is the consistency and accuracy with which a patient follows the regimen prescribed by a physician or other health professional. Compliance is important to insure improved medical care and lower medical costs. The Nursing Standard states that non-Adherence to mediation regimens is a significant problem in older patients, which can lead to therapeutic failure and wastage of medical resources [3]. Gandi found that outpatient drug complications in the ambulatory setting were common, and that this caused an increased use of the medical system which in turn leads to increased cost [4, 5]. Compliance issues are not limited to a specific social economic, educational or cultural level; but affect all cultures [1, 5, 6, 7, 8].

The medical literature indicates that common causes of non-compliance include poor patient memory, physical difficulties, unpleasant side effects of medications, lack of social support, poor and lower education levels, depression, communication problems, medication supply and multiple medications [3, 7, 8, 9, 10, 11]. Several studies show that patients can over utilize or under utilized medications [9, 11, 12]. Golden says that over utilization not only increases medical costs by the patient taking additional medication doses but also increases the risk of adverse drug reactions, for which older patients have an increased risk for [2]. Emergency Medicine Reports estimated that the adverse medication rate for those above the age of 45 is double that of the younger age group [1]. Emergency Medicine Reports have also shown that the medications that older patients are more likely to require, anticoagulants, Antihypertensives, anticonvulsants, digoxin, and anti-inflammatory medications are the medications that are involved in most adverse dosing occurrences [13].

Various methods have been applied to increase patient compliance including verbal and written instructions, home visits, telephone prompting, behavior modification, limited medication access and pill bottle alarms [7, 14, 15]. The International Journal of STD and AIDS states that these methods have met with various degrees of success but to date pill bottle alarms have been the most effective when single medications are involved [6].

Thus, it is evident that a medication delivery system that was able to be accessed easily by the patient, would deliver the right medication at the right time and thus prevent over utilization as well as under utilization would improve medication compliance with increased patient safety by decreasing medication dosage errors and optimize medication utilization would also decrease medical system costs and patient satisfaction. This next level in outpatient medical care can be met by the development of a device that could notify the patient of the appropriate dose of medication at the appropriate time in a manner that the patient with impaired motor ability could access and handle multiple medications. Emergency access would also need to be available. A device that would have these functions would solve many of the compliance issues that have yet to be resolved by other methods.

Elderly and sick people have to take medication due to their ailments or illnesses. Typically, they are prescribed several different types of medication, which must be taken in varying dosages. 25% of the elderly population use four or more prescriptions on a daily basis [16]. Patients must keep track of the correct times in which they are supposed to take these medications. 55% of the elderly fail to comply with medication regiments [16], and 50% of all prescriptions filled are taken incorrectly [17]. Oftentimes, age and sickness take their toll on a person's senses, and it is a common occurrence for individuals on medication to suffer from forgetfulness, lack of concentration, and impaired hearing or sight. Studies show that 43% of the general population make errors in taking medication, 58% of the elderly make errors in taking medication, and of these errors 26% are potentially serious according to their doctors [16]. Unfortunately elderly persons whom live alone often have no one to rely upon but themselves. Keeping track of medication is a very burdensome and often dangerous task for these individuals. There is no reason in this day and age of technology that a device cannot be designed to aid in this important task. Our project will solve the prescription medication compliance problem, which is prevalent among the sick and elderly.

Elderly and sick people suffer from the following problems with taking medication:

Forgetting to take their medication at the proper times.
Taking the incorrect amount of medication at the proper time.
Overdosing their medication by taking it more than once because they forget that it has already been consumed.
Not taking medication on purpose because they are uncertain if they have already taken it.
Remembering which medication is the correct one to take at the proper time.
Attempting to open prescription bottles is difficult due to childproof caps or any hand crippling disease such as arthritis.

Having a loved one go through these difficulties with medication is a taxing experience for family members. Generally, family members are involved in overseeing and aiding a person with his or her medication. 80% to 90% of people requiring care in the US receive it from family members or friends [17]. This care process can be a very time consuming, frustrating, and stressful period for both family members directly and indirectly involved. It is very hard for family members to come into a situation that is alien to them and try to be responsible for a person that may or may not be able to completely communicate all that needs to be done. Having a system that will take care of these problems associated with medication will not only help the patient but also give the family peace of mind.

This SmartPillBox has been designed using knowledge from several fields. These are Computer Science/Information Technology Communication Technology (Interactive voice response, wireless communication, mobile communication, plain old telephony, internet)

Medical Sciences

Microelectronic device design 4.1 The Smart Pill Box as a Solution to the Medical Non-Compliance Problem The invention is part of the solution addressing to the medical non-compliance problem. The medical non-compliance problem is known to be a very important one in the medical field. Patients that are not complying with the medical treatment they have been prescribed are said to be non-compliant.

For many patients it is difficult to remember to take medication prescribed to them. Even if the patients remember to take their medication they often forget whether they took it and may take an extra dose of the medication. Many diseases worsen severely if the patient deviates from the prescribed treatment. The problem of non-compliance is known in the medical field to be a very important one. For serious diseases like diabetes and hypertension it can affect the health of the patient in a severely negative way if the patient is not complying with the treatment. A solution to the patient non-compliance problem benefits millions of patients in the USA.

The SmartPillBox offers an effective solution to the patient non-compliance problem. The functionality of the SmartPillBox will be explained in the next section.

5. BRIEF SUMMARY OF THE INVENTION

Many patients with a serious disease do not comply with the treatment they have been prescribed. Often patients forget to take their medicine regularly. This is often the case for diseases for which there is no instant reaction when the prescribed treatment is not followed. Even if the condition of the disease does not worsen instantly the consequences can still be very severe. An example of this is diabetes. It is crucial the well-being of the patient that he/she is complying with the treatment. Yet the non-compliance rate for diabetes patients goes as high as 50%. Many patients could improve their health and condition of the disease significantly by increasing their medical compliance.

The invention can increase the compliance by helping the patient better manage his health and his compliance to the prescribed treatment. The invention can be connected to a disease management system called Compliance Engine™. The communication with the patient about his health is automatically taken care of by the disease management system once the patient has been registered in the system.

Thus, the system that has been invented offers great value to patients since it is a tool that helps patients improve the condition of most diseases.

The Smart-Pill-Box helps the patient reduce his non-compliance rate by:
1. Keeping track of when he has taken his medication
2. Verifying whether the patient is following the prescribed medication schedule
3. Communicating with the disease management system about the patients compliance
4. If the patient is deviating too much from the medication schedule the disease management system will inform the patient and his nurse, physician or family that he is not compliant and that action needs to be taken to help him.

6. BRIEF DESCRIPTION OF THE FIGURES AND DRAWINGS

Figure 6:
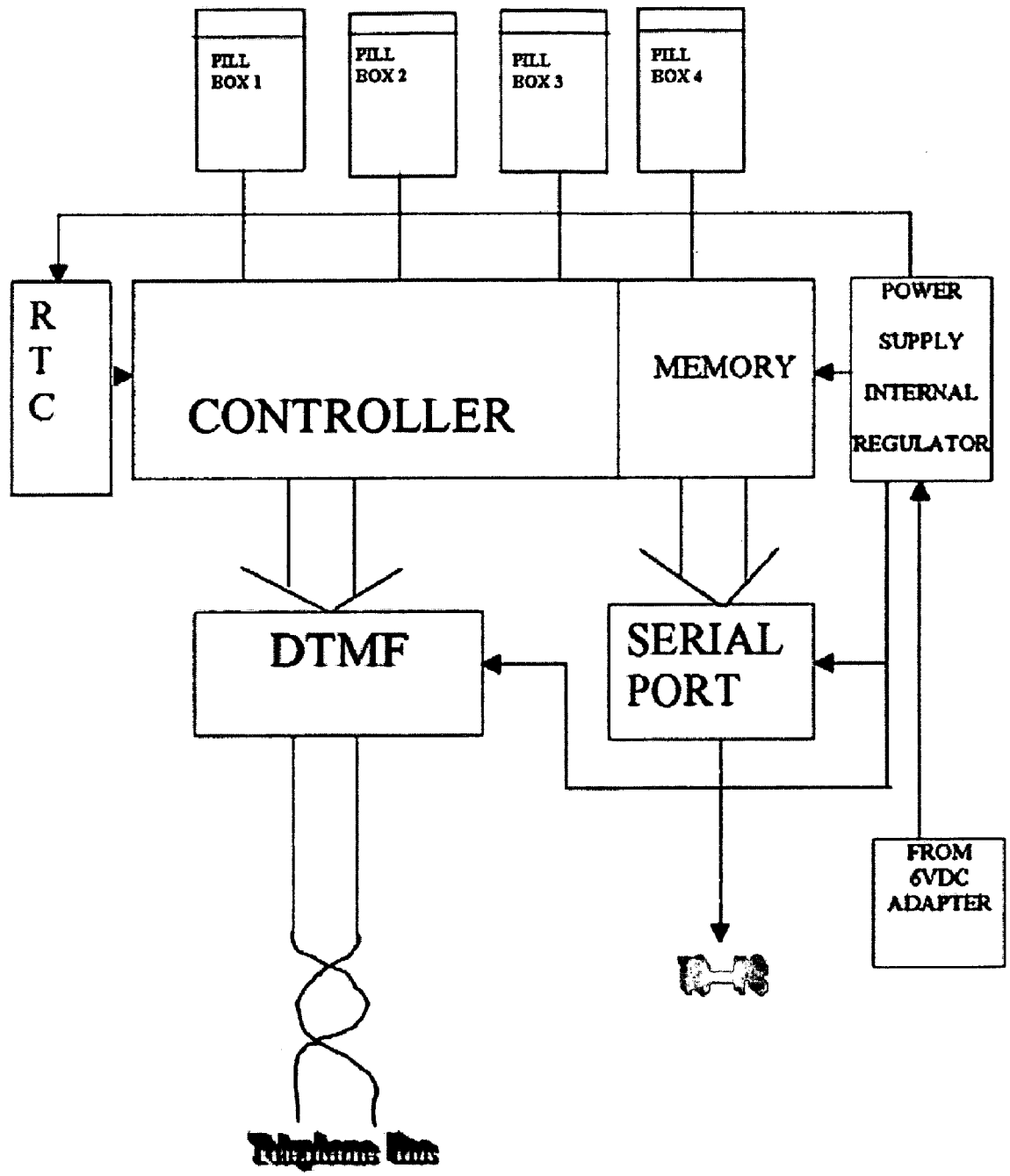

FIG. 6 is an illustration of the block diagram of the Smart-Pill-Box. This diagram explains the design and construction and design of the SPB on a broader level. It uses RTC (Real Time Clock) a processing chip and a memory chip set, power supply etc. There is space for 4 pill box holders in the device. The weight sensors for each of the pill box are connected to the controller. The controller sends and received information from a disease management system over the phone line. There is a serial port, a DTMF, a RTC and an external power supply. There is also a rechargeable battery backup in case of power cuts.

Figure 7:
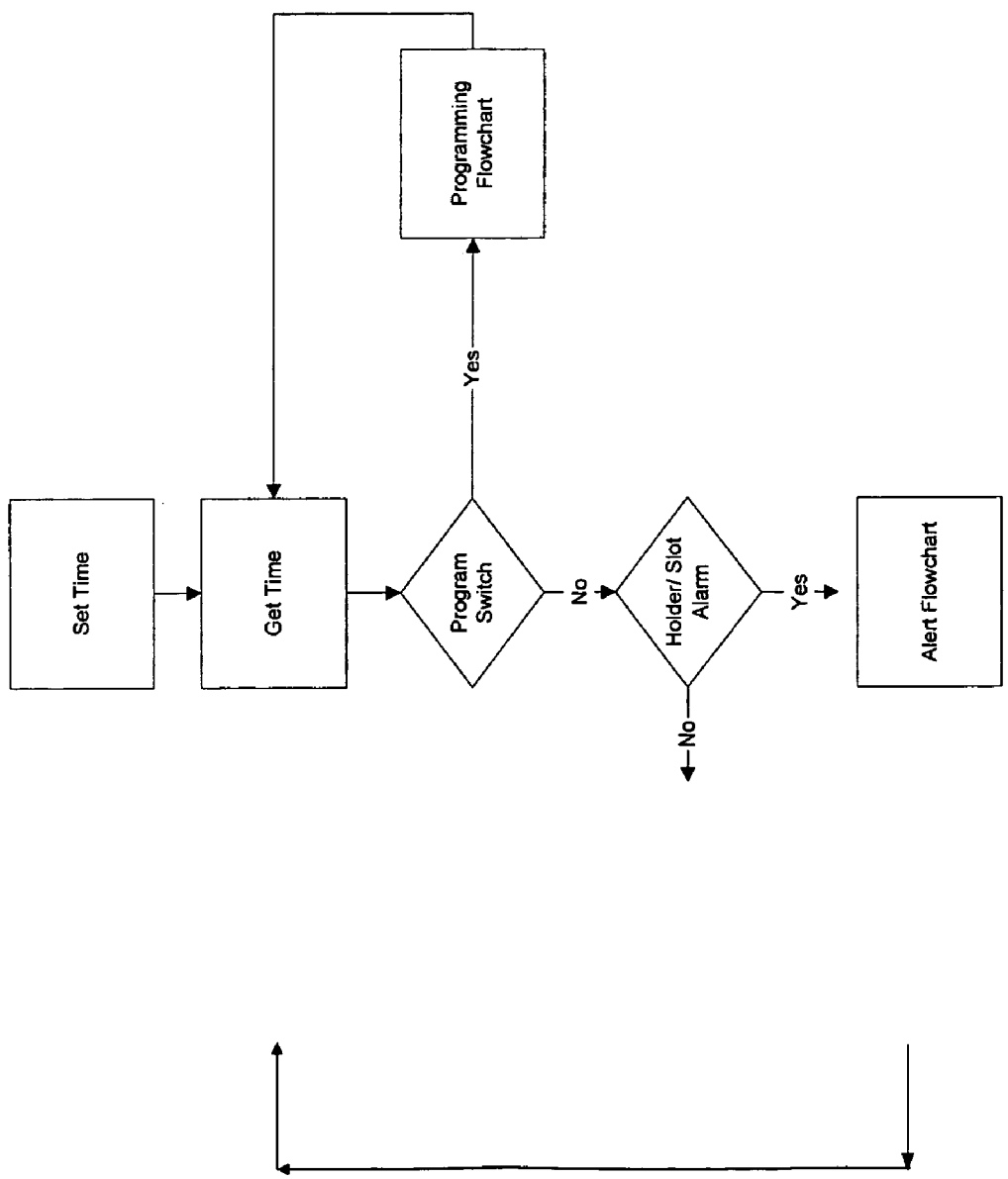

FIG. 7 is an illustration of Smart-Pill-Box Main Flow Chart

Figure 8:
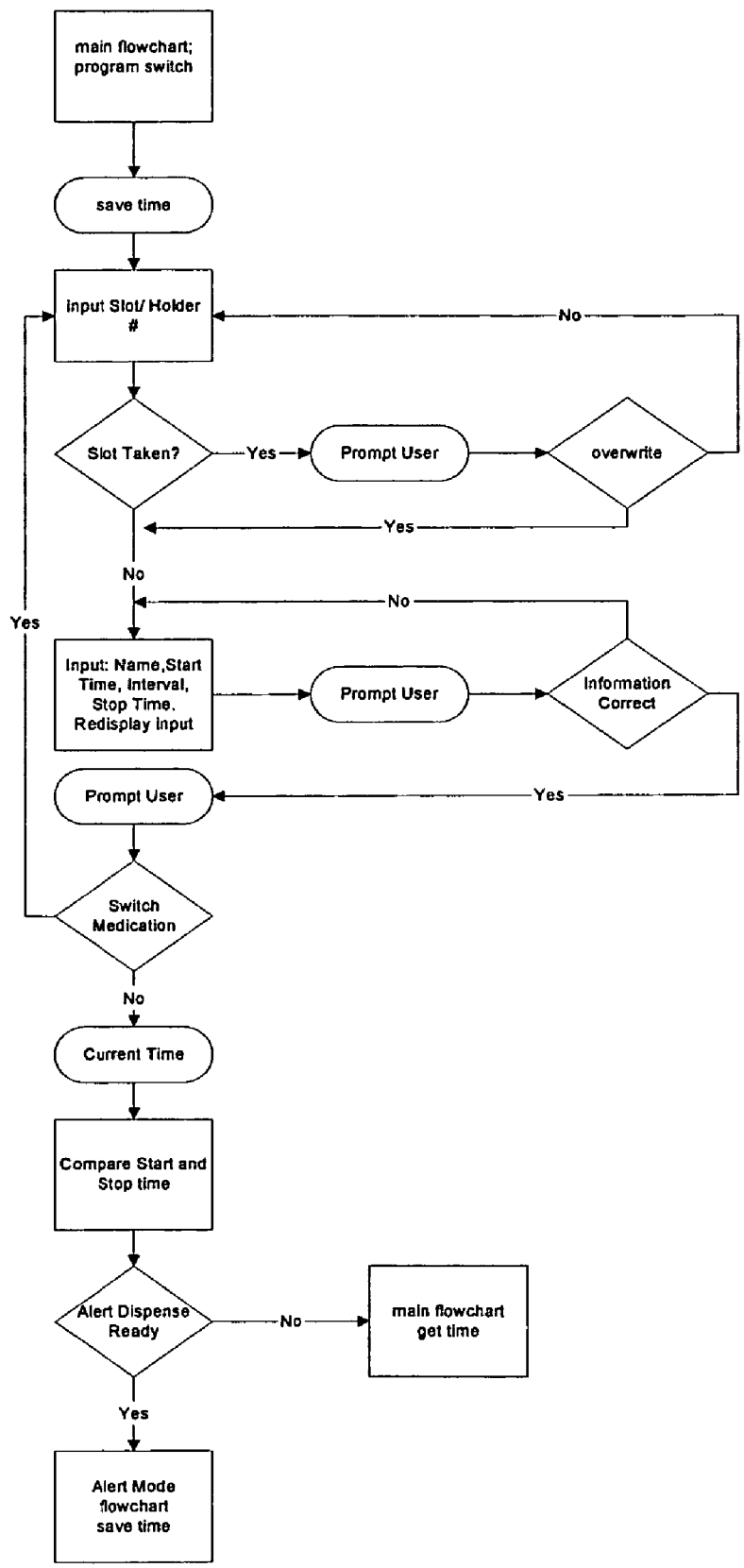

FIG. 8 is an illustration of Smart-Pill-Box Programming Mode Flow Chart

Figure 9:
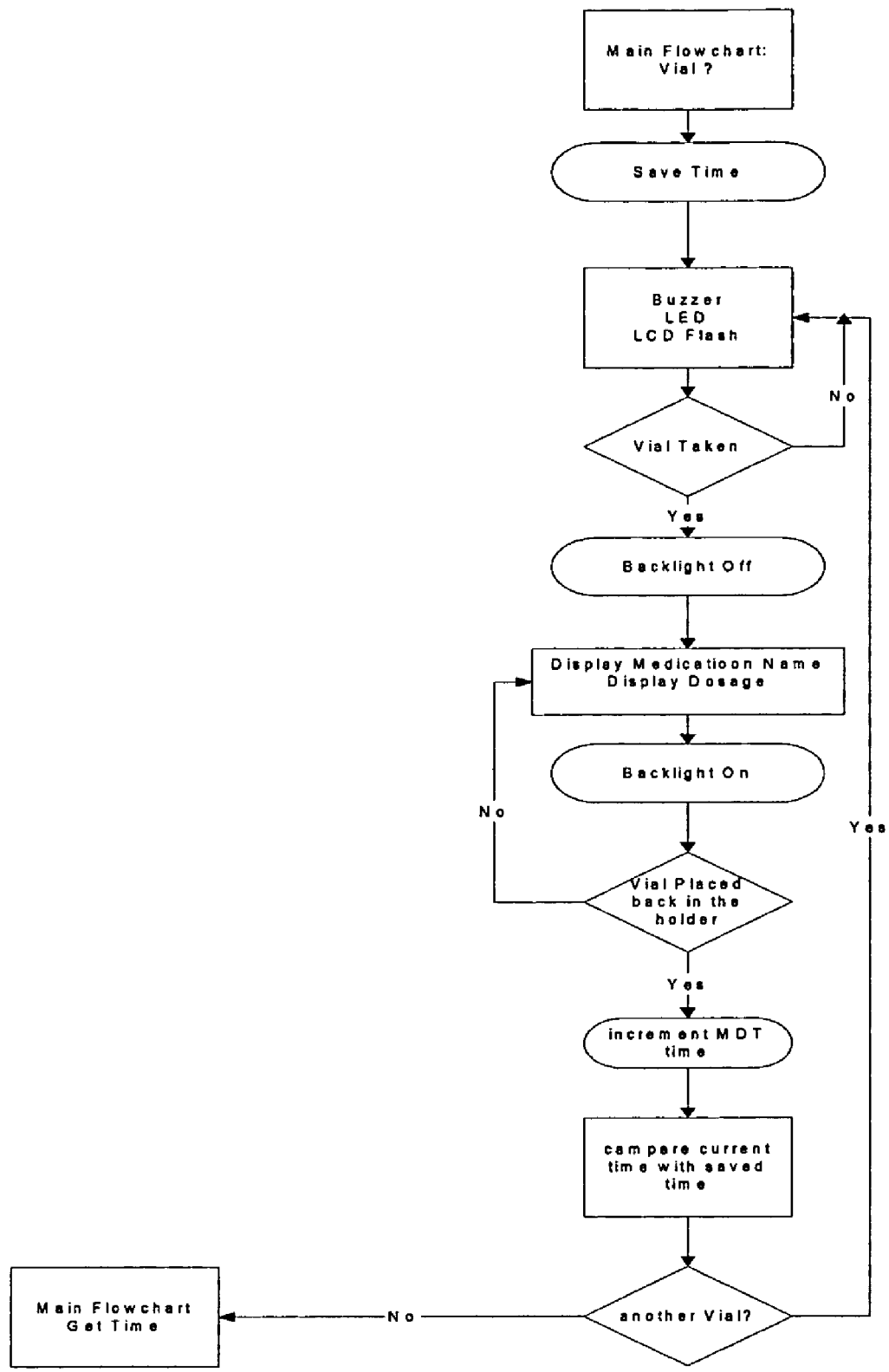

FIG. 9 is an illustration of Smart-Pill-Box Alert Mode Flow Chart

Figure 10:
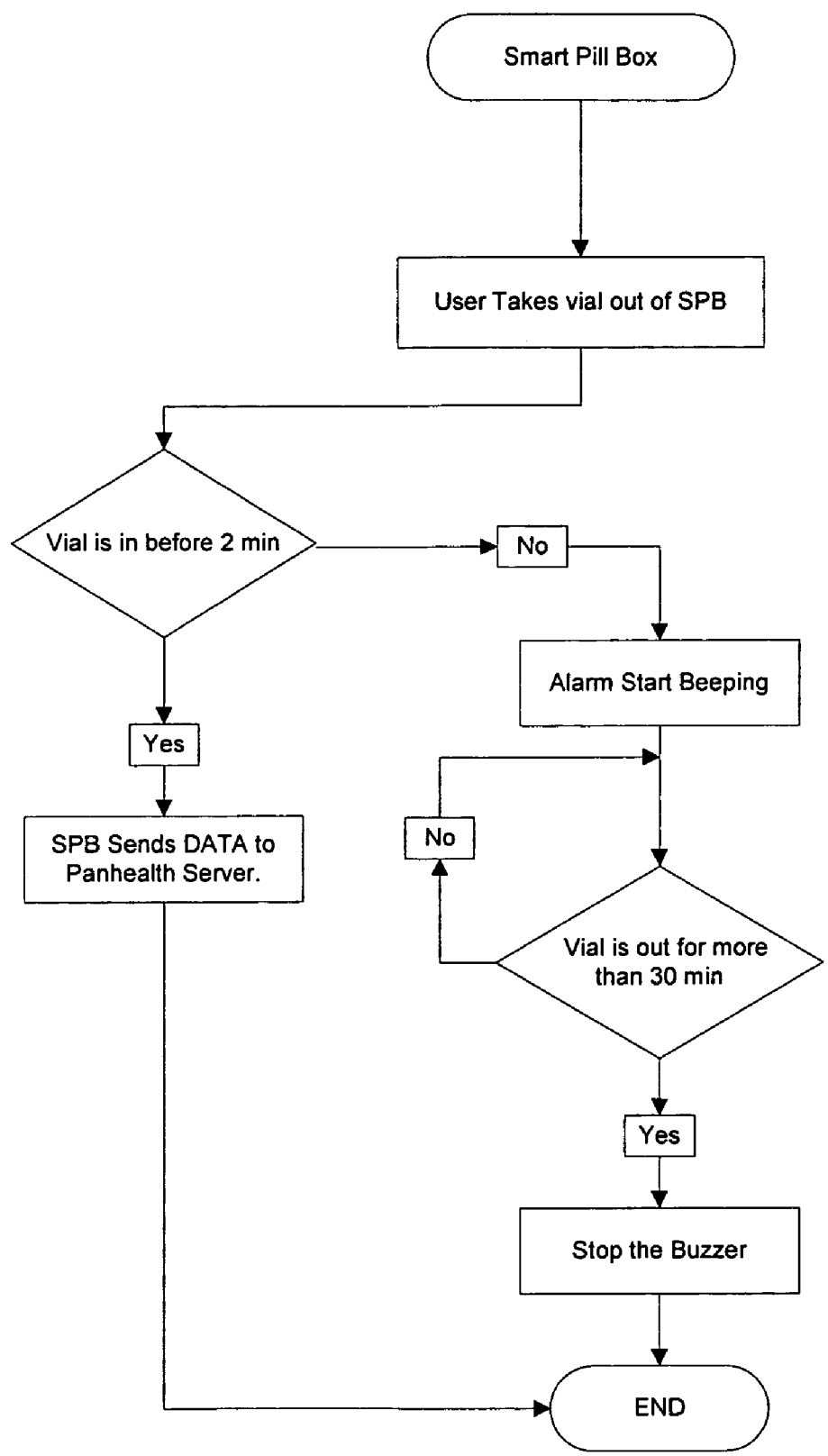

FIG. 10 is an illustration of Smart-Pill-Box Alert Mode Flow Chart Module-1

Figure 11:
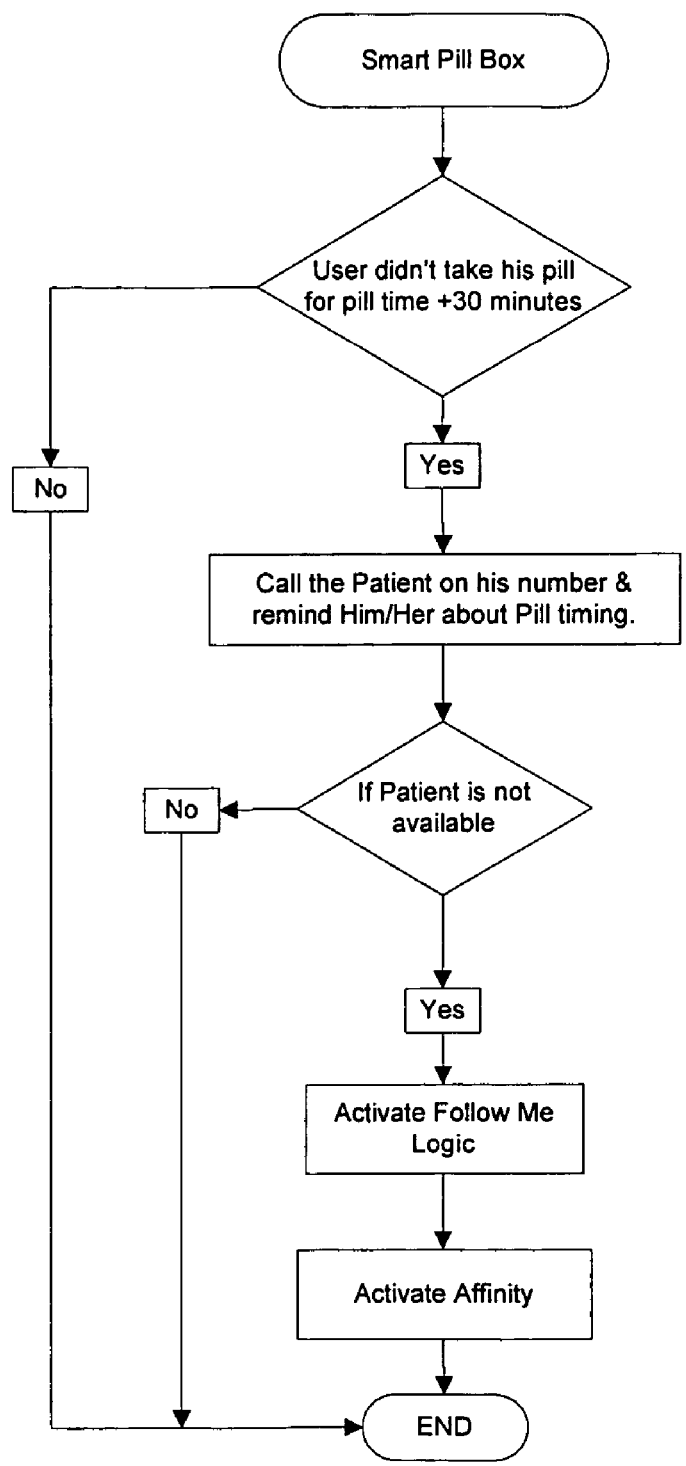

FIG. 11 is an illustration of Smart-Pill-Box Alert Mode Flow Chart Module-2

Figure 12:

FIG. 12 is an illustration of PDA Keyboard Byte Data Format

FIG. 13 is an illustration of the physical design of the Smart-Pill-Box

7. DETAILED DESCRIPTION OF THE INVENTION

Medical non-compliance is a serious problem for patients in the USA. In the table below it can be seen that many patient are not complying with their medication schedule. As an example 50% of Diabetics do not follow the medication schedule their physician has prescribed for them.

TABLE 1

Rate of Non-Compliance in the USA

| Disease | Rate of Non-Compliance in the USA (NIH and CDC) |
|---|---|
| Diabetes | 40% to 50% |
| Hypertension | 40% |
| Arthritis | 55% to 71% |
| Epilepsy | 50% |

TABLE 1-continued

Rate of Non-Compliance in the USA

| Disease | Rate of Non-Compliance in the USA (NIH and CDC) |
|---|---|
| Organ Transplant | 18% |
| Asthma | 20% |

The above diseases are serious diseases yet patients do not comply with the treatment they have been prescribed. One reason for this could be that there is not an instant reaction when the prescribed treatment is not followed. Even though the condition of the disease does not worsen instantly the consequences can still be very severe in the long run. Diabetes is one such case.

The invention helps patients improve their health by increasing their medical compliance. The invention increases the compliance by helping the patient better manage his health and supervise his medical compliance.

The invention can be connected to Compliance Engine™ and work as a part of this system. In this set-up
1. The patient's physician lays out the medication schedule that the patient should follow and is supervised by the disease management program.
2. The Smart-Pill-Box takes care of measuring the patient's medication consumption. The Smart-Pill-Box forwards this information to the disease management system.
3. The disease management system uses the information to find out whether the patient is compliant with his medication schedule.
4. If he is not compliant the disease management system takes action to encourage the patient to take his medication.

All communication between the patient and the disease management system works to implement the physician's advice yet without using the physician's time. In this way the system work as a extension of the physicians arms.

The invention helps patients manage their health and diseases more effectively than what is possible without the invention. The disease management system gathers information from patients, health care providers and people otherwise related to the patient. The information is gathered using a variety of communication methods. Information about the patient and the treatment that he/she should comply with is stored in the system. As an example some information is gathered automatically by calling the patient reminding and inquiring him about his compliance to the treatment. Information about the treatment can be stored by the patient's physician using the internet. The disease management system integrates all the patient's health information and uses this to create a customized algorithm for managing his disease and treatment.

In sum, the system that has been invented offers great value to patients since it is a tool that helps patients improve the condition of most diseases.

7.1 Functionality of the Smart-Pill-Box

As explained in the previous section the patient non-compliance problem is an important problem that is key to the health of millions of patients. The SmartPillBox offers a solution to the patient non-compliance problem. The SmartPillBox keeps track of how many pills the patients have taken and when these were taken. This invention is therefore capable of improving patients' health significantly.

The functionality of the SmartPillBox is based on a weight and a microprocessor keeping track of time and the number of pills left at any time in the SmartPillBox The patient's schedule for taking his medication is also stored. The SmartPillBox uses this information to infer whether the patient is complying with his treatment. If he is not he will be reminded by the SmartPillBox to take his medication. All information can be forwarded to a system called Compliance Engine™, another invention by undersigned inventor.

The SmartPillBox works in the following way:
1. The SmartPillBox is filled with the prescribed medicine
2. The schedule for the medicine consumption is stored in it.
3. The weight of the total number of pill is weighed automatically by SmartPillBox and stored.
4. Each time a pill is taken, the SmartPillBox will register the change in weight of the pills and use this information to mark the time the pill was taken and from the change in the weight of the remaining pills calculate how many pills were taken.
5. The SmartPillBox can remind the patient to take his medication. Further SmartPillBox can send information using a telephone line to external systems to store the information of the patient's compliance. This information will be acted upon by the external system. For example the system can alert a nurse or physician if the patient is not compliant.

7.2 Construction of the Smart-Pill-Box

The purpose of this invention is to build an intelligent SmartPillBox. A pharmacist or family member will program the device. When the programmed time has been reached, an audio alarm will sound and a visual alarm will light up, the patient will lift the pill box to consume the needed medication, and the medication name and dose amount will be displayed on the LCD.

Smart Pill Box design consists of slots/holders for holding pill boxes of various sizes. Each slot has photoelectric sensors on two sides. These sensors are used to sense whether the pill is the slot or it have been picked up by the patient. These sensors send the electronic signals to the processor/IC chip. The Smart Pill Box has a telephone jack that can be used to connect the Smart-Pill-Box to the telephone line. It also has a reset button that can be used to wash of the data from the IC and bring the SPB to normal state. The SPB has inbuilt removable battery power supply.

7.2.1. Medication Support

The medication will be taken from the Pill-box inserted in the holders/slots mounted on the top of the device. The device will have support form one to many different medications because the elderly and sick usually are prescribed more than one medication to keep up with and take. The average number of medications by each patient over the age of 60 years in the American Geriatrics Society study was greater than 5 per day [2]. Each SmartPillBox will have vials of various sizes. Specified vial sizes are as follows: 1) 50 mm 2) 45 mm 3) 40 mm 4) 30 mm 7.2.2. Dispensing Scheme At the time of Pill to be taken as per the scheduled program: respective vial LED indicator will give green flashing signal with discontinued beep sound. This indicated that the person has to take the prescribed pill. If the pill box is lifted after this signal then the green flashing LED will glow continuously green with no beep sound. (This will indicate that the person is talking the pill). After 20 seconds the same LED will turn red. This means that the person has to keep the vial back in the Smart-Pill-Box unit. If the pill vial is not placed back in to the SmartPillBox unit before 2 min. then respectively LED will give red flashing signal with continuous beep sound. But if the person keeps back the vial within 20 sec. then Smart-Pill-Box assumes that the pill has not been consumed. At the same time respective vial LED indicator will give green flashing signal with discontinued beep sound. If the person keeps the vial back after 20 sec. Smart-Pill-Box records that pill has been consumed and sends the data to server through telephone line. Once it is recorded that the pill has been taken the LED indication in front of that pill vial will glow continuously red till the next pill taken time as per schedule program. If the person tries to take this vial out within scheduled program time then Smart-Pill-Box will give beep sound alert to the person that this medicine is not to be taken. Lastly when the next programmed time has been reached, the red LED automatically turns to green flashing with an audible alarm.

7.2.3. Real-Time Clock

A real-time clock will be used to make sure the device alerts the user to take his or her medication at the appropriate time, and that the medication is dispensed in a timely fashion. The clock will be accurate. The real-time clock and 32 MHz crystal will be connected to the microcontroller through an $I^2C$ bus. The time will be set upon system power up.

7.2.4. Alarms

The device has both audio and visual alarms because the user may have either a hearing or sight impairment. When it is time to take the medication, a single LED will light up, the buzzer of the device will sound, and the LCD will flash. All alarms will cease once the dispense button is pressed.

7.2.5. Power

The device will be powered by a 9 VDC source. A 120 VAC-9 VDC converter will be used as a primary power supply, and a 9V alkaline battery will be used as a secondary power source. The 9V battery backup will have a battery life of approximately 6 hours. The backup battery will power the system in case the power goes out or if the user wants to travel with it thus making the device portable. A single 9V battery will be used as a backup power source. The device will use a single 9V battery instead of AA batteries for the following reasons:

- A 9V battery provides sufficient levels to power the 5V regulator, solenoids, and LCD.
- One 9V battery is equivalent to 6 AA batteries.
- One 9V battery is half the cost of 6 AA batteries.
- A 9V battery will last at least 6 hours based on a 100Ω load and running the battery to a voltage of 5.4 volts.

7.2.6. Packaging

The device's dimensions will be 200 mm. (W)×45 mm. (H)×100 mm. (D) and approximately 1.5 lbs in weight (size and weight varies as per the change in the number of vial holders). This device is designed to be portable. The components of the device will be strategically mounted to the device for easy access. The LCD will be mounted in a raised position for easier viewing. The vial slots/holders will be structured around the LCD. The LED will be positioned in the front of the device for bettering viewing. The programming button will be located at the front of the device as well for easy access. The keyboard will be attached to the bottom of the device in the front. It will slide out and the user can then unfold the keyboard. The serial port for CPU programming will be located on the right side of the device.

7.2.7. LCD (Liquid Crystal Display)

The LCD screen will be used as an interface when programming the device. It will display all the options/menus for programming the device's times, dosages, and names of the medications. The LCD will display the name of the medication, and how much of that medication to take. The LCD will be positioned in the back center of the device at a titled angle for optimal viewing. The LCD is a standard 24 character by 4-line backlit display. It uses a serial connection to receive data from the microcontroller to display the medication information.

7.2.8. Keyboard

The main function of the keyboard will be programming the device. The SmartPillBox will use of a Membrane/Tacktile PDA keyboard for its size, compactability, and input capabilities. It will allow the user to easily input the medications, name, dosage, and times. It will be attached to a chaise in the bottom of the device. It can be pulled out of the device and unfolded anytime the device needs to be programmed. The keyboard should only be accessed for programming purposes. Not all of the keys on the keyboard will be recognized by the microcontroller in order to minimize the overhead associated with programming the device.

7.2.9. Serial Programming

The user will have the ability to program the device using a CPU instead of with the onboard keyboard. The main reason for this option is so the device can be programmed using a GUI instead of the LCD interface. The device will communicate with the CPU through a RS232 serial cable.

7.2.10. Programming

The user will program the device whenever the system switch is set to programming mode. The user will be prompted to input the vial number, medication name, dosage amount, start time, interval time, and end time. After the user has inputted these parameters, they will be redisplayed and the user will be asked for their correctness. The start time is the time when the user should first take the medication each day. The interval time is number of hours from when a medication is taken to when it should be taken again. The end time is the last time a user should take his or her medication for a day. This will allow the user to sleep without being woken up by the alarms. The device can be programmed both onboard and offboard. The user will use the LCD and PDA keyboard for onboard programming, and the user will use a serial connection and GUI for off board programming.

7.3. Approach

Elderly, sick, and mentally handicapped people have to take multiple medications to deal with their ailments. Keeping track of these medications is very burdensome and can be life threatening. This invention will attempt to assist these people in taking the correct dosage at the appropriate times. The SmartPillBox will have the capability to dispense up to five different medications. It will alert the user to take the medication through audio and visual alarms. These alarms will go off at the time to take the medication programmed by the user. The medication name and dosage amount will be displayed during pill consumption. The pills will be retrieved from the holders.

7.4 Hardware Approach

Figure 1:
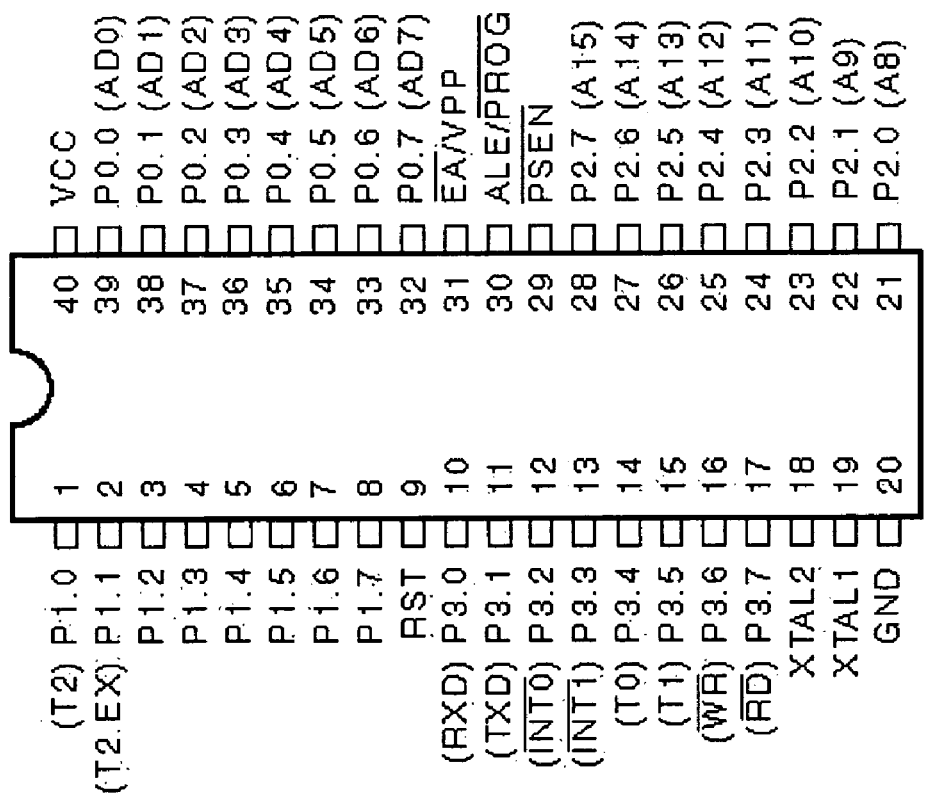
FIG. 1 is an illustration of the Atmel AT89C52 Controller Board

The heart of the project is the Cypress AT89C52 microcontroller. The pinout of the chip after being programmed for the SmartPillBox can be found in FIG. 1. In it you can see the UART ports for serial communication, and the $I^2C$ bus. You can also see the various control lines for all the components.

Another key component to the SmartPillBox is the dispensing mechanism. Smart Pill Box design consists of slots/holders for holding pill boxes of various sizes. Each slot has photoelectric sensors on two sides. These sensors are used to sense whether the pill is the slot or it have been picked up by the patient. These sensors send the electronic signals to the processor/IC chip. The Smart Pill Box has a telephone jack that can be used to connect the Smart-Pill-Box to the telephone line. It also has a reset button that can be used to wash of the data from the IC and bring the SmartPillBox to normal state.

Figure 2:
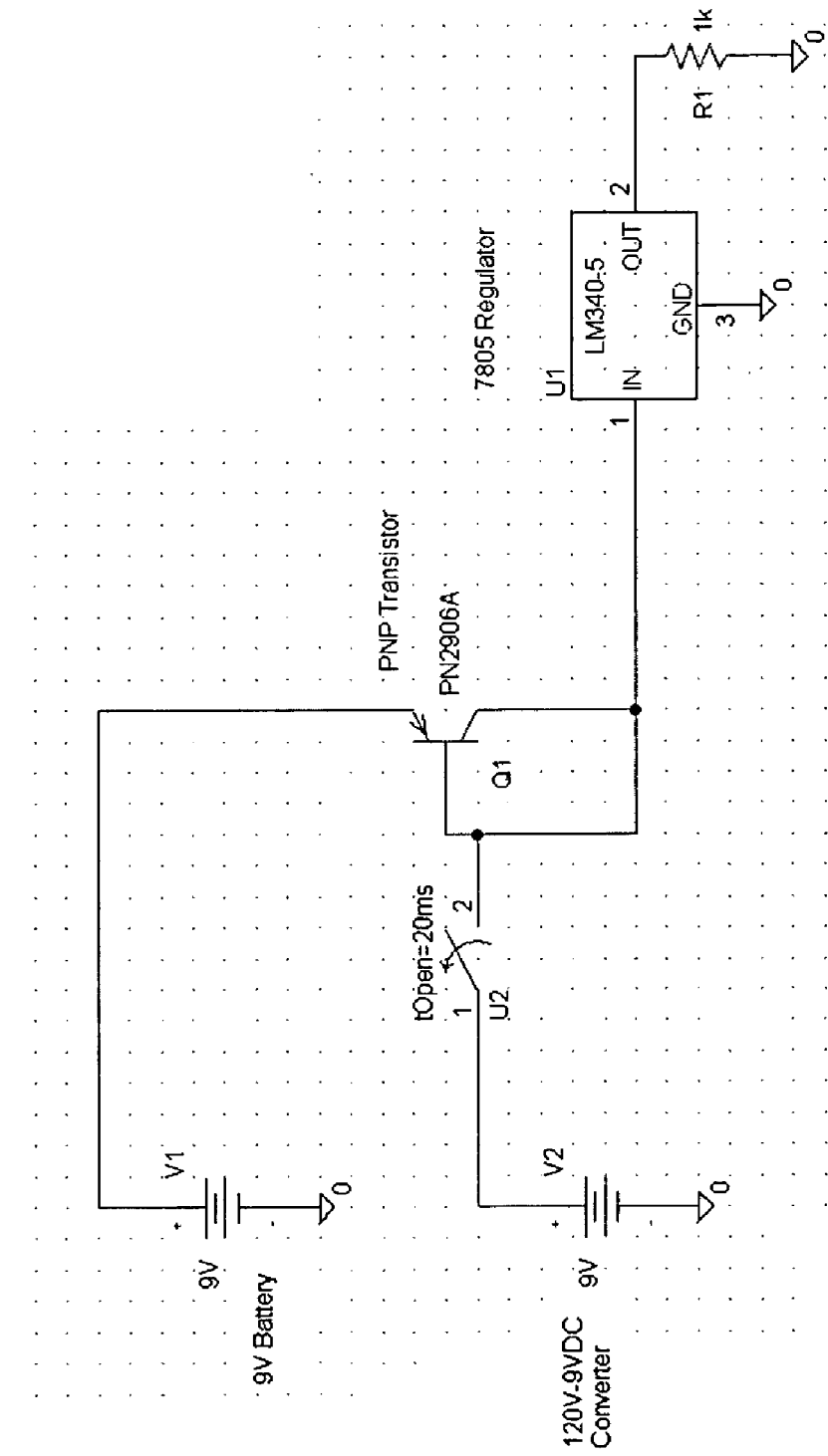
FIG. 2 is an illustration of the Backup Battery Schematic

In case of a power outage the SmartPillBox will have a backup battery that can run the system until power is restored. This way if the power goes out the user can still be dispensed medication. There will be no drop out from switching from the main power to the backup and vice versa. The schematic for the backup battery can be found in FIG. 2.

Figure 3:
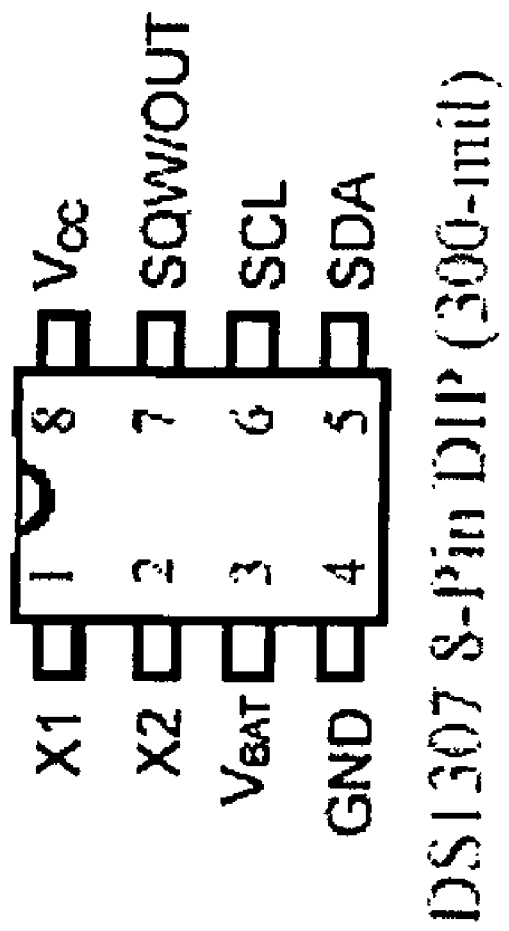
FIG. 3 is an illustration of DS1307 Real-Time Clock Pinout
Figure 4:
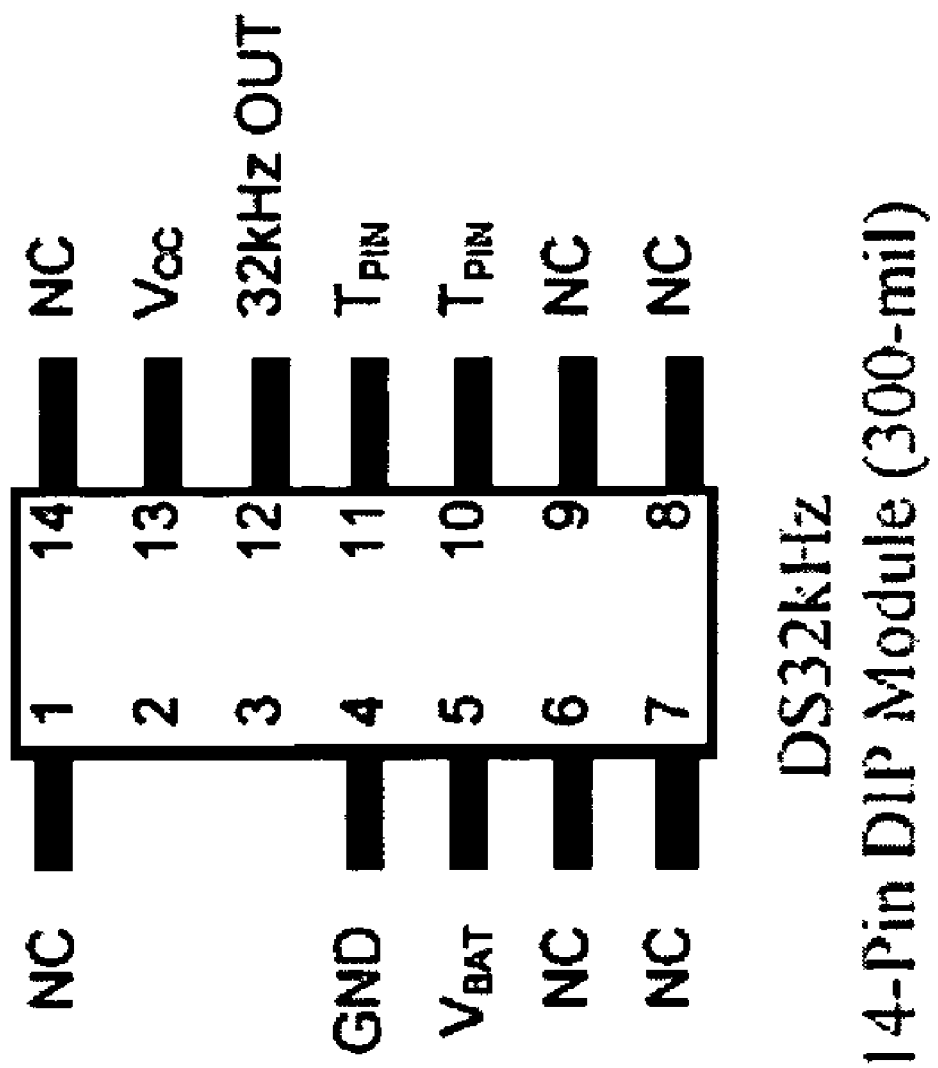
FIG. 4 is an illustration of 32 KHZ Crystal Pinout
Figure 5:
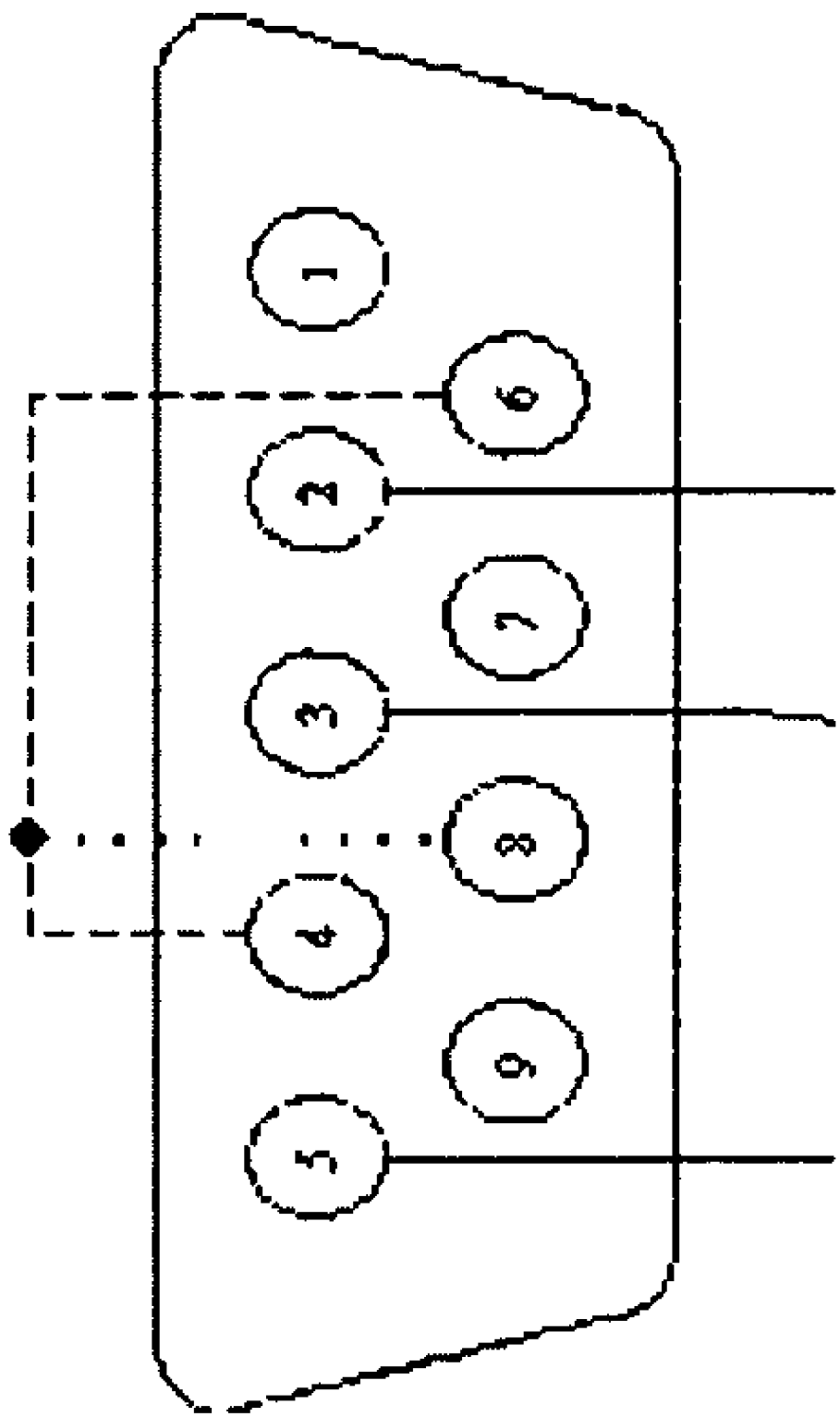
FIG. 5 is an illustration of RS232 Pinout

The real-time clock will be interfaced with using I²C bus communication. This format is easy to implement and occupies few pins on the microcontroller. It also keeps very accurate time when interfaced with 32 KHz crystal. The pinout for the real time clock can be found in FIG. 3-4, and the pinout for the 32 KHz crystal can be found in FIG. 3-5. Another reason this format was chosen for the real-time clock is that several team members have experience using it from Micro II.

The SmartPillBox can also be programmed by a CPU through a serial cable. To communicate serially with the CPU we chose to go with RS232 format. The pinout for the RS232 can be found in FIG. 5. Serial communication is an easy to implement format that does not require too many pins on a microcontroller.

To get a better overall idea of the SmartPillBox system and its components refer to FIG. 6. This system diagram shows all the major components of the AMDS and how they are connected.

7.5 Software Approach

All the code written for the Atmel AT989C52 microcontroller for this invention was done in 'Assembly' program language.

The SmartPillBox will have two modes of operation, dispensing mode and programming mode. These will be determined by the system switch. Upon system power up the user will be asked to input the time. Note that when entering the time for one's digit values that the ten's digit should have a zero placed in it. When inputting in a time the user will be prompted to press 1 for AM and 2 or PM. When the system switch is set to programming mode the user can program the device to dispense a medication. If the system switch is not in programming mode, the system will constantly be checking to see if an slot/holder alarm time has been reached. If an alarm time had been reached the system goes into alert mode. Switching between these two modes is the responsibility of the main, which can be shown in FIG. 7.

The SmartPillBox can be programmed by the setting the system switch to program mode. The user is first asked to enter in the slot/holder number that they want to program. If the slot/holder is already programmed the user is asked if they want to overwrite the existing program. If the user does not wish to overwrite the existing information they can select another. The user then prompted to enter the medication name. After the name has been inputted it is redisplayed to the user for correctness. If the name is not correct the user must input it again. After the name has been inputted the user is asked to input the medication's dosage amount. The user is then redisplayed what he or she entered and asked if it is correct. If it is not correct the user can input in the correct dosage amount. The user is then prompted for the start time. The start time is the first time during the day when a user should take his or her medication. It is typically when the user wakes up in the morning. The user is then asked to verify the correctness of the start time. If the start time is not correct the user can input the correct start time. The user is then asked to input the interval time. The interval time is the time in between when a pill is taken and when it should be taken next. Note this interval can only be inputted in as hours. The user is then asked to verify the correctness of the interval time. If the interval time is incorrect the user can input in the correct one. After that, the user is prompted for the end time. The end time is the last time during the day in which the user should take his or her medication. This is typically when the user goes to bed. The user is then asked whether or not the end time is correct. If it is not correct, the user can enter in the correct end time. Lastly, the user is redisplayed all the parameters he or she has entered in and asked to verify their correctness. After programming one slot/holder the user has the option to program another, if not the program returns to main. If an alert alarm time has occurred while the user has been programming the device the system will go into alert mode once the system switch is set off of programming mode. Note that the backspace, delete, and arrow keys do not work. If the user has encountered an error in inputting a parameter he should input it again upon data verification. When inputting in a time the user will be prompted to press 1 for AM and 2 or PM. The flowchart for programming mode can be found in FIG. 8.

Once an alarm time has been reached the system goes into alert mode. First the alarms will go off alerting the user that it is time to take his or her medication. The alarms will not cease until the vial is lifted from the holder. During this time the buzzer sounds, the LED lights up, and the LCD flashes. Once the vial is lifted from the holder the medication name, and dosage are written to the backlit screen, this information is also then sent to the centralized server into the disease management system. The program will then wait for the vial to be placed back in the holder, assuming the user has take his or her medication. The system will then check to see if another slot/holder alarm time has been reached. If so alert mode will be repeated all over again. If no other medication is to be taken the time is then redisplayed on the LCD and the program returns to main. Alter mode module-1 can be better visualized using FIG. 9

The user also has the option to program the SmartPillBox using a GUI on a CPU. The SmartPillBox will communicate to the CPU through a serial connection. The GUI will allow the programming of the device to be less tedious. The following FIG. 10 and FIG. 11 are the alert model flow charts demonstrating smart-pill box communication with the Compliance Engine disease management system.

The user makes use of a PDA keyboard to program the device onboard. The keyboard uses TTL level communication but does not send ASCII characters but instead sends X and Y coordinates. The keyboard sends one byte of data upon key depression, and sends another byte of data upon key release. The X coordinate consists of three bits, while the Y coordinate consists of four bits. FIG. 3-11 shows the format of the keyboard data.

The I²C bus real-time clock returns its values in BCD format. To display characters on the LCD they need to be in ASCII format. Therefore, a BCD to ASCII converter was written to overcome this obstacle and allow the microcontroller to communicate with the real time clock. This was an essential key in having the capability to set the time and to get the time.

Incrementing the time also proved to be a challenge. The real-time clock had to be told if it was in 12 hour or 24 hour mode. This was done by setting a bit in the byte data stream. Our system always operates in 12-hour mode so the bit always needed to be set. The AM and PM had to be kept track especially when the alert alarm time was supposed to rollover. Also the time had to be programmed to rollover correctly once it went past 12 at anytime. A function called increment was created to take care of all these parameters.

The Atmel AT89C52 has capabilities of implementing a full duplex UART (Universal Asynchronous Receiver Transmitter). For our project the UART was used in communicating with components serially. The UART was used in interfacing to the CPU, and to the PDA keyboard. This capability of the microcontroller made using serial communication much easier, and significantly contributed to our project.

7.6. Test Specifications

The SmartPillBox will be tested using various test processes and tools. Each individual functionality will be thoroughly tested. The table below displays the equipment and processes by which we will test all functions of the AMDS. These test will be performed and evaluate at different times during the course of the design.

TABLE 2

Test Requirements

| Requirements | Digital Multimeter | C Compiler | Oscilloscope | Simulator |
|---|---|---|---|---|
| LCD Interface | | X | | X |
| Accuracy of Real Time Clock | | | X | X |
| LED Visual Alarm | X | | | X |
| Audio Alarm | X | | | X |
| Vial Sensor | X | | | X |
| Keyboard | | X | | X |
| Power Source | X | | X | |

7.6.1 LCD Interface

A compiler and debugger/simulator will be used to verify LCD code correctness. Once the LCD code has been compiled and tested in software, it will be uploaded to the Atmel AT89C52 microcontroller. During usage, the LCD will be tested to display the medication's name, and the correct dosage. During programming, the LCD will be tested to prompt the programmer for the following items:
- a slot/holder (1-5) to hold the medication
- the name of the medication
- a dosage amount for the medication
- a start time for taking the medication each day
- a time interval in hours for which the next dosage should be taken
- an end time for taking the medication each day

7.6.2 Accuracy of Real Time Clock

The real time clock of the Atmel AT89C52 microcontroller will be connected to an oscilloscope. The waveform of the clock will then be analyzed for accuracy against a known time period. The $I^2C$ bus communication will be tested for accuracy to make sure it is properly communicating with the microcontroller.

7.6.3 LED Visual Alarm

The voltage across the LED will be measured using a digital multimeter. A voltage will be measured across a known resistance. The current will be determined using the voltage obtained from this known resistance. The current will then be compared to current specifications to make sure it is within the tolerances of the LED. The LED of each slot/holder will be tested. The LED should light up at the programmed dispense times. Voltage will be supplied to the LED when the real time clock reaches the programmed alert time. Testing the LED will occur in the following three stages:
- Testing that the microcontroller outputs an activation signal to the transistor at the correct time
- Testing that the current through provided by the transistor in operation is within the allowed specifications for the LED
- Inserting the LED into the system after passing the first two tests and checking that it operates properly within the system

7.6.4 Audio Alarm

The voltage across the buzzer will be measured using a digital multimeter. The known resistance of the buzzer will be used with this data to calculate the power being consumed by the buzzer to make sure that the values are within the tolerances of the buzzer. The buzzer should light up at the programmed dispense times. Voltage will be supplied to the buzzer when the real time clock reaches the programmed dispense time. The voltage will cease once the user has pressed the dispense button. Testing the buzzer will occur in the following three stages:
- Testing that the microcontroller outputs an activation signal to the transistor at the correct time
- Testing that the current through provided by the transistor in operation is within the allowed specifications for the buzzer
- Inserting the buzzer into the system after passing the first two tests and checking that it operates properly within the system

7.6.5 Vial Sensor

The Vial sensor will be tested using the continuity checking function of the digital multimeter. When the vial is placed in the slot/holder, the resistance across the two pins of the lid sensors should be negligible. When the vial is lifted from the holder/slot, the resistance should be infinite. If multiple medications need to be taken, the closure of a lid will indicate to the controller that it needs to open the next lid in the medication sequence.

7.6.6 Keyboard

The keyboard will be tested and simulated in software first using a C compiler. Then the keyboard will be connected to the microcontroller and ran through the different states. The functionality of each key will be tested. Some keys should have no functionality at all.

7.6.7 Power Source

The power source will be tested with an oscilloscope to ensure that the signal is clean and is configured in a DC waveform. The digital multimeter will be used to verify that the power source is at the correct voltage level. The 9V DC backup battery will be tested to ensure that it has a battery life of six hours. To perform all these tests the power source will be hooked up to an emulated load.

I claim:

1. A system for dispensing at least one or more pill medicines to a patient comprising:
   a pill box comprising one or more medicine vials and a microprocessor in communication with the pill box's real time clock, keyboard, telephone jack, audio alarm indicator, and one or more light-emitting diode (LED) alarm indicators corresponding to the one or more medicine vials;
   the pill box microprocessor is configured to receive schedule data, via the keyboard, including a patient's schedule for taking the at least one or more pill medicines, and time data via the real time clock;
   the pill box stores patient medicine including at least one or more pill medicines in one or more of the medicine vials;
   the pill box telephone jack connects the pill box to a telephone line over which the patient's compliance information can be sent an external system for storage or for alerting a nurse or physician that the patient is not compliant;
   the pill box microprocessor is configured to instruct at least one medicine vial's respective LED alarm indicator to flash a green signal, and the audio alarm indicator to emit alert sounds, in response to the real time clock indicating the scheduled medication dosage time, which designates that the patient is to take the indicated one or more pill medicines;

the pill box microprocessor is configured to instruct the at least one medicine vial's respective LED alarm indicator to signal continuously green, and the audio alarm indicator to not emit alert sounds, in response to the at least one vial being taken from the pill box before the real time clock has indicated that 20 seconds has passed since the scheduled medication dosage time, which designates that the patient should be taking the one or more pill medicines;

the pill box microprocessor is configured to instruct the at least one medicine vial's respective LED alarm indicator to signal red in response to the real time clock indicating that 20 seconds has passed since the scheduled medication dosage time, which designates that the patient should put the at least one medicine vial back in the pill box;

the pill box microprocessor is configured to instruct the at least one medicine vial's respective LED alarm indicator to flash a red signal, and the audio alarm indicator to emit a continuous alert sound, in response to the at least one medicine vial not being placed back in the pill box after 2 minutes since the scheduled medication dosage time;

the pill box microprocessor is configured to instruct the at least one medicine vial's respective LED alarm indicator to flash a green signal, and the audio alarm indicator to give a continuous alert sound, in response to the at least one medicine vial being replaced within 20 seconds of the scheduled medication dosage time, which designates that the patient has not consumed the one or more pill medicines;

the pill box microprocessor is configured to record that the one or more pill medicines have been consumed by the patient and sends the data to a server through the telephone lines in response to the one or more vials being placed back in the pill box after 20 seconds from the scheduled medication dosage time;

the pill box microprocessor is configured to instruct the at least one medicine vial's respective LED alarm indicator to signal continuously red until the next scheduled pill medicine dispensation time occurs, per the received scheduled data, in response to recordation at the server of the one or more pill medicines having been taken by the patient; and the pill box microprocessor is configured to instruct the audio alarm indicator to sound an alert in response to a vial being taken out at an unscheduled time, which designates that the patient is not to take any medicine.

2. The system of claim 1, wherein the pill box further comprises one or more slots for holding the one or more medicine vials, wherein the one or more slots include photoelectric sensors on two sides to sense whether a pill medicine vial is in a slot or has been removed from the pill box.

3. The system of claim 1, wherein the microprocessor receives data without use of the pill box's keyboard by communicating with a CPU through a RS232 serial cable.

* * * * *